United States Patent [19]

Goepp et al.

[11] Patent Number: 4,517,970
[45] Date of Patent: May 21, 1985

[54] CONFORMING VALVED CERVICAL CAP ASSEMBLY AND IN-SITU MOLDING METHOD

[75] Inventors: Robert A. Goepp, Chicago; Uwe E. Freese, Oak Park; Marvin P. Loeb, Chicago, all of Ill.

[73] Assignees: University Patents, Inc., Westport, Conn.; Contracap, Inc., Schaumburg, Ill.

[21] Appl. No.: 510,278

[22] Filed: Jul. 1, 1983

Related U.S. Application Data

[62] Division of Ser. No. 207,904, Nov. 18, 1980, Pat. No. 4,401,534.

[51] Int. Cl.³ .............................................. A61F 5/46
[52] U.S. Cl. ................................................... 128/131
[58] Field of Search ............... 128/127, 128, 129, 130, 128/131

[56] References Cited

U.S. PATENT DOCUMENTS

| 3,952,737 | 4/1976 | Lipfert et al. | 128/127 |
| 4,007,249 | 2/1977 | Erb | 128/131 |
| 4,198,965 | 4/1980 | Strickman et al. | 128/127 |
| 4,320,751 | 3/1982 | Loeb | 128/127 |

Primary Examiner—Richard J. Apley
Assistant Examiner—Carolyn Harrison
Attorney, Agent, or Firm—Dressler, Goldsmith, Shore, Sutker & Milnamow, Ltd.

[57] ABSTRACT

A conforming valved cervical cap assembly is provided with an elastomeric inner layer molded and cured in situ adjacent the exocervical surface of a cervix uteri. The inner layer is wettable, non-porous and matingly fits and resiliently complements the exocervical surface. In order to prevent the molding material from clogging or otherwise impairing operation of the valve, a valve cover is detachably connected to the valve during molding and curing.

18 Claims, 11 Drawing Figures

CONFORMING VALVED CERVICAL CAP ASSEMBLY AND IN-SITU MOLDING METHOD

This is a division of application Ser. No. 207,904, filed Nov. 18, 1980, now U.S. Pat No. 4,401,534.

TECHNICAL FIELD

This invention relates to contraceptive devices, and more particularly, to a cervical cap assembly and method of molding the same to conform to the shape of the cervix uteri.

BACKGROUND OF THE INVENTION

Caps for cervix uteri as birth control devices are well known and have been found among the artifacts of antiquity. It has been reported that Aetius of Amida suggested for this purpose the use of the skin of a pomegranate cut into a hollow cup and that beeswax discs fashioned to fit over the cervix have been used in Europe.

Conventional cervical caps are made in many sizes to accommodate the various cervix sizes normally encountered, however, with such caps the fit for a particular individual is usually inexact and probably a compromise. Usually the cervix is either wedged into the cap or a compressive retainer or clamp is utilized. As a result, conventional caps often become dislodged during normal body movement, and particularly during coitus, and have to be removed periodically to accommodate normal uterine discharges.

Typifying the many types of cervical caps that have been developed are those shown in U.S. Pat. Nos. 2,836,177, 3,952,737 and 4,007,249, and German Patent No. 475,496 as well as in *Das Weibliche Gebar-Unvermogen by F. A. Wilde in Berlin in* 1838 according to U.S. Pat. No. 4,007,249. These cervical caps have met with varying degrees of success. In particular, the cap shown in U.S. Pat. No. 4,007,249 is made while the wall of the vagina is expanded by means of a speculum. Such an expedient tends to deform the cervix and thus precludes a good fit between the cap and the cervix. Additionally, medical grade silicone rubber, the material of choice in said patent for making the cap is not readily wettable, thus surface tension cannot be relied upon to hold the cap properly in place on the cervix. In addition, some medical grade silicone rubbers are porous, and cervical mucous, uterine discharges and bacteria are likely to accumulate in the pores, thereby causing unpleasant odor, in addition to a risk of infection. In such instances, cervical caps may be usable only for limited time period, e.g., about 6-8 hours.

It is therefore desirable to provide an improved cervical cap with an inner wettable liner that is impermeable or non-porous, and which conforms to the cervix uteri of the female for whom the cap is made, so that the surface tension created by a layer of mucous between the inner wettable surface of the cap and the exterior of the cervix will hold the cap in place and prevent dislodgement during intercourse or customary physical activities.

SUMMARY OF THE INVENTION

An improved cervical cap assembly is provided which is custom-fit, comfortable, durable, reliable and effective. The novel cervical cap assembly remains in place during vigorous sexual intercourse as well as during normal body movement, since it conforms to the surface of the cervix and enjoys the holding force of surface tension, and can be comfortably worn for extended periods of time, such as months or even years, without removal.

The cervical cap assembly is provided with a one-way valving means which permits egress of uterine discharges but prevents ingress of sperm. The cap assembly includes a prefabricated non-porous shell provided with a soft resilient elastomeric lining which is secured to the shell and defines a wettable, non-porous contact surface contoured to matingly fit and resiliently complement the exocervical surface of the cervix uteri while accommodating the usual cyclical configuration changes of the cervix. The valving means includes an aperture at about the apex of the shell and a flexible web overlying the aperture and coacting with the shell. In one form, a removable outer liner sheath is used to separate the cervix from an inner wettable elastomeric material during the molding and curing process. In another form, the inner elastomeric material is non-wettable and is permanently covered by a wettable outer liner sheath that is substantially contiguous with the exocervical surface of the cervix uteri to obtain the desired surface tension effect. In both instances, the defined contact surface is non-porous.

The present cervical cap assembly provides a passive cervical cap, i.e., a cap that exerts no pressure on the cervix when in place. The cap, while in place, is capable of limited sliding movement over the surface of the cervix and exerts no localized pressure on the cervix, thereby avoiding hypertrophy, hyperplasia, dyskeratotic changes in the squamous epithelium, and the like.

In order to custom-fit and contour the cervical cap assembly, the elastomeric layer is molded and cured in situ adjacent the exocervical surface of the cervix uteri of the female who is to wear the cap. A liner or plug covers the valve during molding and curing to prevent the elastomeric layer from clogging or otherwise impairing operation of the valve. The plug can be a T-plug, a bridge plug or an umbrella plug that is preferably removed from the valve after the elastomeric layer has cured. In the preferred method, the flexible outer liner sheath separates the inner wettable elastomeric layer from the exocervical surface during the in situ molding and curing process. After the elastomeric layer has cured, the liner sheath is trimmed or removed.

A more detailed explanation of the invention is provided in the following description and appended claims taken in conjunction with the accompanying drawings.

DETAILED DESCRIPTION OF THE PREFERRED EMBODIMENTS

Figure 1:
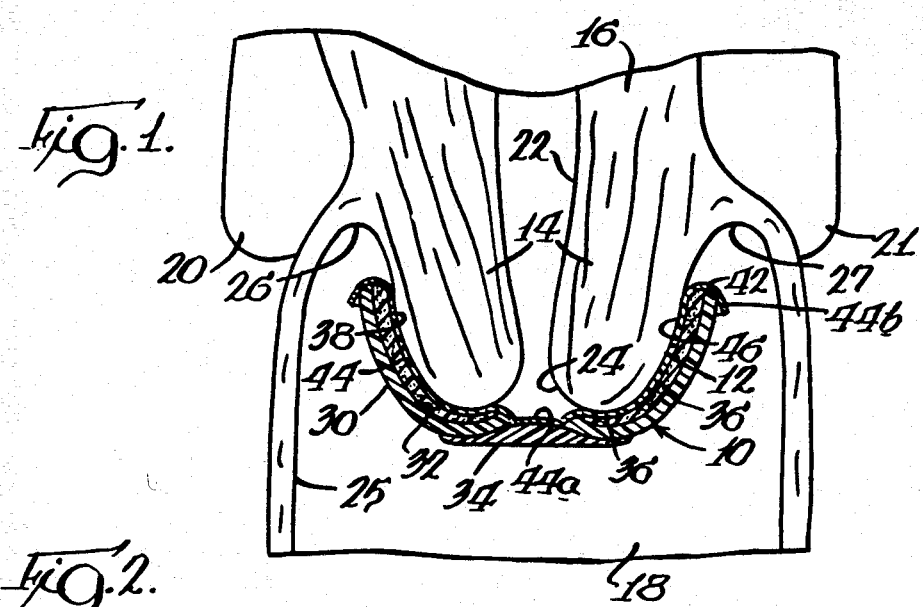
FIG. 1 is a cross-sectional view of a cervical cap assembly being molded and cured in situ contiguous with the exocervical surface of the cervix uteri and with an outer liner sheath which can be removed or trimmed in accordance with principles of the present invention.

Referring to FIG. 1 of the drawings, a custom-fit cervical cap assembly 10 is shown being molded and cured in situ on the exocervical surface 12 of the cervix uteri 14, i.e., on the portio vaginalis cervicis or that portion of the uterus 16 that protrudes into the vagina 18, of the woman who is to wear the cervical cap assembly and for whom the cervical cap assembly is being custom fitted and contoured. The uterus 16 is supported by broad ligaments 20 and 21 and defines fundus that terminates in the cervical os 24. The vaginal wall 25 together with cervix 14 defines the fornices vaginae, i.e., the lateral fornices 26 and 27 as well as the anterior and posterior fornices (not shown).

The cervical cap assembly 10 provides a non-invasive birth control device which is effective and reliable to substantially deter impregnation. Assembly 10 includes a flexible and deformable cervical cap or shell 30 which is preformed. Shell 30 is non-porous and can be dome-like and having a slightly flattened apex, or cup-shaped, with a concave inner surface 32 and a central valve opening or aperture 40 at its apex. Shell 30 is deeper than the cervix uteri.

Shell 30 is operatively connected to a one-way valving means 34 which defines a tunnel or channel that permits unidirectional flow in the direction away from the cervical os 24 but not in the reverse direction. Valving means 34 opens under minimal predetermined positive pressure, which may be 5 millimeters of mercury or less, to permit the outflow of uterine discharges, such as menstrual flow, mucus, and the like, without disturbing the positioning of the cervical cap, but prevents the entry of sperm therethrough into fundus 22. Cervical cap assembly 10 is of a sufficient depth to receive a major portion but not all of the cervix uteri 14.

A soft, pliable intermediate resilient elastomeric contact layer or cushion 36 of a wettable, non-porous material is moldably or adhesively bonded or otherwise attached to the concave inner surface 32 of shell 30. Elastomeric layer 36 has a custom-fit contoured surface 38 which is permanently shaped and contoured to matingly fit and resiliently complement the exocervical surface 12 of the cervix uteri 14. In the preferred embodiment, elastomeric layer 36 extends from a position adjacent valve opening 40 (FIG. 2) to a position adjacent margin or rim 42 of shell 30. Elastomeric layer 36 is sufficiently flexible, compressible and form-assuming to accommodate the usual cyclical configuration changes that the uterus and the cervix undergo.

Figure 2:
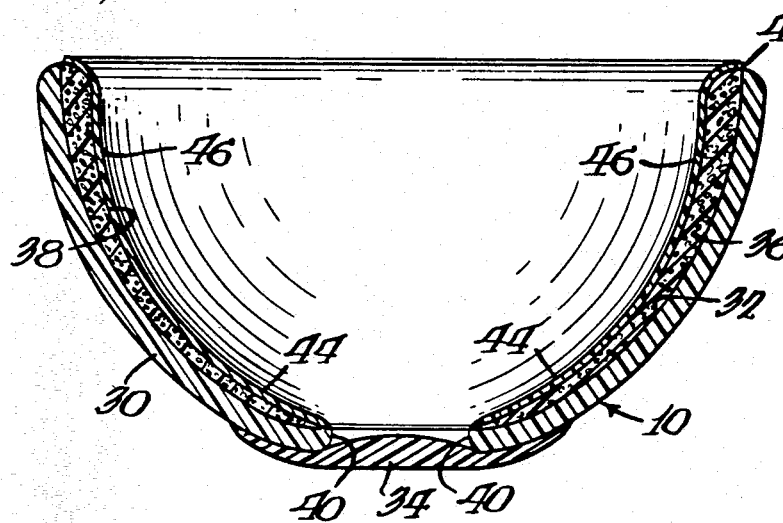
FIG. 2 is an enlarged cross-sectional view of a cervical cap assembly with a trimmed wettable liner sheath embodying the present invention.

As best shown in FIG. 2, a removable protective flexible sheet-like liner or liner sheath 44 isolates and separates elastomeric layer 36 from the exocervical surface 12 (FIG. 1) of the cervix uteri 14 during molding and curing. Liner sheath 44 is moldably or adhesively bonded or otherwise connected to the concave inner surface 32 of shell 30 adjacent valve opening 40 and extends to and is connected against the inner edge of rim 42 so as to completely cover elastomeric layer 36. Liner sheath 44 has valve covering portions 44a which protectively covers valve opening 40 and valve 34 during molding and curing. Liner sheath can also extend over rim 42 so as to form a graspable collar 44b. Liner sheath 44 is made of a flexible, medical-grade, liquid-impervious material which is durable and resistant to tearing. After molding and curing, liner sheath 44, including section 44a thereof, is removed. Cap assembly 10 fits onto the cervix uteri 14 and is slidably held in place by the surface tension of mucous discharge that flows generally continuously from the cervical os 24 along the exocervical surface 12 of the cervix uteri 14 and acts on wettable elastomeric layer 36. In this manner, removeable liner sheath 44, provides a cervix uteri-engaging means that does not exert localized pressure on the cervical surface in contact therewith. In the preferred embodiment, the combination of wettable elastomeric layer 36 and shell 30 exhibits a resiliency that does not deform or distort the cervix uteri 14. Preferably layer 36 and shell 30 are made of the same liquid impervious, non-porous material or of moldably bondable compatible materials.

In some circumstances it may be desirable to use a permanent, wettable, non-porous liner sheath which covers and is moldably bonded, adhesively connected or otherwise permanently secured to a non-wettable and/or porous elastomeric layer. In such cases the elastomeric lining of the shell is constituted by the elastomeric layer as well as the liner sheath. Care should be taken, however, to remove valve covering portions 44a or to sever the valve covering portion 44a from liner sheath 44 about valve opening 40 to assure operability of valving means 34. In such circumstances, the outer liner sheath 44 and intermediate elastomeric layer 36 together provide a multi-layer, resilient elastomeric lining having a non-porous and wettable contact surface.

The preferred method to make, custom fit and contour the cervical cap assembly 10 to the exocervical surface 12 of the cervix uteri 14 is to completely cover valving means 34 and valve opening 40 with portions 44a (FIG. 1) of liner sheath 44 and to bond or otherwise attach the peripheral part of those valve covering portions 44a to the concave inner surface 32 of cervical cap 30 about valve opening 40. For added securement, valve covering portions 44a can also be bonded or otherwise attached to valving means 34.

Liner sheath 44 is positioned along the concave inner surface 32 of preformed shell 30 so that its unattached portions 44b are spaced inwardly of the cap's rim 42 to form an elastomeric material-receiving pocket, opening, spacing or cavity between the concave inner surface 32 of cervical cap 30 and liner sheath 44. The pocket is then filled with a wettable paste-like elastomeric-forming material which is moldable and curable at about body temperature to form elastomeric layer 36.

After the pocket has been filled with elastomeric material, to which the catalyst or curing agent has been added, the free end or distal end 44b (FIG. 1) of liner sheath 44 is turned over the edge of rim 42 and may be bonded or otherwise attached to rim 42 or left free. In order to insert the cap assembly in the vagina, the wall of the vagina is initially expanded with vagina speculum blades to facilitate access and to expose the exocervical surface 12 of the cervix uteri 14. The cap assembly is then inserted in the vagina until the liner sheath 44 is firmly positioned against the exocervical surface 12 of the cervix uteri 14. Liner sheath 44 prevents the paste-like elastomeric-forming material from physically contacting the exocervical surface 12 of the cervix uteri 14.

The speculum, when in position, pulls on the ligaments supporting the uterus and cervix and thus distorts the cervix uteri. Therefore, it is important to remove the speculum from the vagina or to close the speculum blades so as to permit the cervix to return to its normal, undistorted configuration before the paste-like material has taken a permanent set.

The paste-like material is molded and cured in situ adjacent the exocervical surface, on the pocket side of liner sheath 44, to form wettable elastomeric layer 36 which generally conforms to, matingly fits and resiliently complements the natural, undistorted exocervical surface 12 of the cervix uteri 14. The curing temperature can be slightly above the body temperature so long as the exocervical contacting surface 46 of liner 44 is at a comfortable temperature to the person being custom fitted with the cervical cap assembly 10 during in situ molding and curing.

After layer 36 has cured or set, the term "set" being used herein interchangeably with the term "cured", assembly 10 is removed from the vagina and the excess portions of liner 44 extending over rim 42 are trimmed or, in the case of liner 44 extending over rim 32 to form the graspable collar 44b, said liner 44 is detached. The valve aperture-covering portions 44a of liner 44 are thereby removed to provide a cap assembly 10 as shown in FIG. 2.

Liner sheath 44 and shell 30 can be adhesively connected to elastomeric layer 36 before molding or after curing if they are not connectable thereto during the molding process. Alternatively, liner 44 can be directly bonded or otherwise attached to the inner surface of shell 30 to securely entrap, enclose and wedge the unattached elastomeric layer 36 between the liner sheath and the concave inner surface 32 of cap 30 without exposing the seam of the bond. Shell 30 is preformed in various sizes so that a shell size providing the desired thickness of layer 36 can be selected for a given user. The valving means can be prefabricated with the shell. Of course, removal of liner sheath 44 necessitates that elastomeric layer 36 be liquid impermeable when cured. Any minor surface imperfections in layer 36 that are noticeable after liner sheath 44 is removed can be filled in, using the same curable material that is used for forming layer 36 initially or in any other convenient manner.

While the above cervical cap assembly 10 is preferred, in some circumstances it may be desirable to use a non-wettable and/or porous elastomeric material to form layer 36 and to permanently retain wettable, non-porous liner 44 after the elastomeric layer 36 has been cured. In such a case a wettable, non-porous outer liner sheath material and a non-wettable elastomeric material may be used together as indicated above. Because of the novel custom fit and contoured method of in situ molding and curing described above, liner 44 sheath is composed of a medical grade, liquid-impervious, non-porous material which is generally unabrasive and non-irritating to the wearer, directly contacting the exocervical surface of the cervix uteri.

Alternatively, use of liner sheath 44 can be confined to covering valving means 34 and valve opening 40. The wettable, non-porous elastomeric material 36 can be activated by mixing with an activating agent or catalyst, and an ample amount of same is spread around the inner surface 32 of cap 30, after which the cap assembly 10 is inserted onto the cervix during the curing process. After curing, cap assembly 10 is removed, liner sheath 44 is detached and any excess portion of layer 36 is removed by trimming. The cap is then reinserted.

The cervical cap assemblies of FIGS. 3-11 are substantially similar to the cervical cap assembly of FIGS. 1 and 2 except as explained below. For ease of understanding and for clarity, similar parts and components of the cervical cap assemblies of FIGS. 3-11 have been given part numbers with the same last two digits as similar parts and components of the cervical cap assembly of FIGS. 1 and 2.

Figure 3:
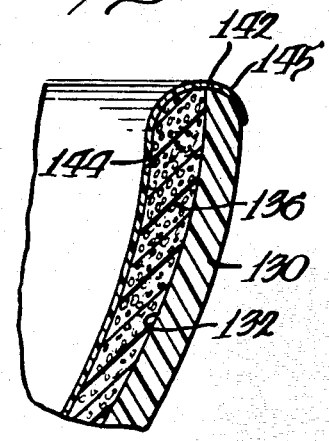
FIG. 3 is a fragmentary cross-sectional view of portions of another cervical cap assembly in accordance with principles of the present invention.

In the embodiment shown in FIG. 3, the distal end 145 of liner sheath 144 is bent over the rim or skirt 142 of shell 130 and bonded or otherwise secured to rim 142 after the elastomeric layer 136 has cured and the cap assembly removed from the vagina. The excess portions of liner sheath 144 are then trimmed.

Figure 4:
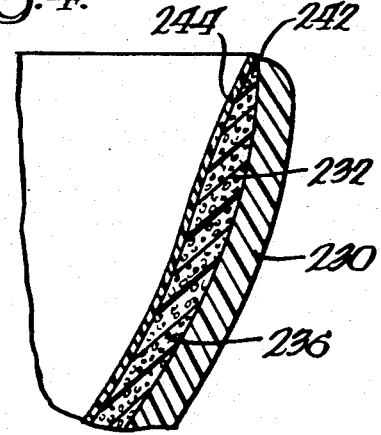
FIG. 4 is a fragmentary cross-sectional view of portions of still another cervical cap assembly in accordance with principles of the present invention.

In the embodiment of FIG. 4, liner sheath 244 is bonded or otherwise secured to the inside edge of rim 242. The resultant cured layer 236 has a narrow beveled and wedge shape of reduced thickness adjacent rim 242 as compared to a more rounded shape shown in the previous embodiments.

Figure 5:
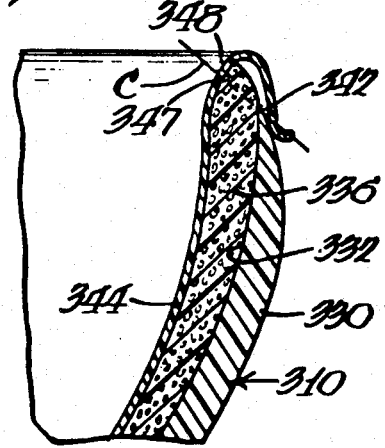
FIG. 5 is a fragmentary view of portions of a further cervical cap assembly manufactured in accordance with the present invention but before final trimming.

In the embodiment shown in FIG. 5, liner sheath 344 extends beyond rim 342 and is reverse bent, forming a pocket, to be attached by adhesive or otherwise bonded to the rim 342 of exterior of shell 330. The cervical cap assembly 310 is inserted onto the cervix and molded and cured in situ as explained above. After the moldable material forming layer 336 has been cured, the cap assembly 310 is removed and the excess elastomeric material 336 as well as excess liner margin 348 are cut and removed along the severance line C to form an inwardly converging tapered surface or end portion 347 having a generally frusto-conical configuration, which extends beyond shell 330 and can be cut with a series of slits to form deformable sections, as hereinafter described. Any remaining portion of liner sheath 44b can be detached. As a result, the peripheral marginal portion or rim of cap assembly 310 is thinner than the average wall thickness of the cap assembly and is beveled toward the fornices when the cap assembly is in place.

In the embodiment of FIG. 5, shell 330 has a tapered body 348, which is beveled or tapered towards rim 342, with a maximum thickness of about 0.2 millimeters at rim 342. Other thicknesses can be used. If desired, the cervical caps of the other embodiments of this invention can also have a tapered body.

Figure 6:
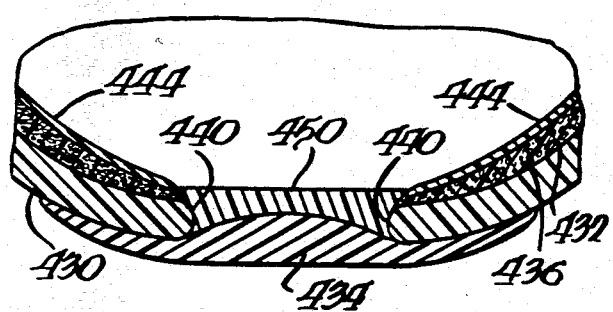
FIG. 6 is a fragmentary cross-sectional view of portions of a cervical cap assembly which has been fitted with a canal button or plug and liner sheath for in situ molding and curing in accordance with principles of the present invention.

In the embodiment of FIG. 6, a canal button or plug 450 is used in lieu of valve aperture-covering liner portions 44a (FIG. 1). Plug 450 is positioned in the valve opening 440 and bonded or otherwise removably secured to valve means 434 before the moldable elastomeric-forming material is poured into the pocket between the concave inner surface 432 of cervical cap 430 and liner sheath 444. Plug 450 is substantially solid and covers valve means 434. After plug 450 is attached to valve means 434, liner sheath 444 is adhesively connected to plug 450, if it is not integrally connected thereto, before the moldable material is poured into the pocket. After the moldable material has been poured into the pocket, the free end of liner sheath 444 is bent over rim 42 and the cap assembly is positioned over the cervix and molded and cured in situ as described with respect to FIG. 1. When the moldable material has cured, the cap assembly is removed from the cervix, the excess liner extending over rim 442 is trimmed and secured to rim 442, if it is not already moldably bonded to rim 442, and plug 450 is removed.

Figure 7:
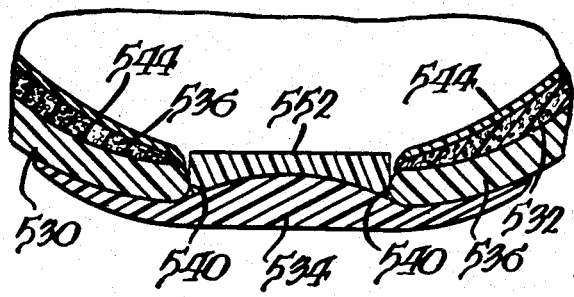
FIG. 7 is a fragmentary cross-sectional view of portions of a cervical cap assembly fitted with another plug and liner sheath for in situ molding and curing in accordance with principles of the present invention.

The method shown in the embodiment of FIG. 7 is substantially similar to the embodiment of FIG. 6, except that canal button or plug 552 is separate from and not connected to liner sheath 544.

Figure 8:
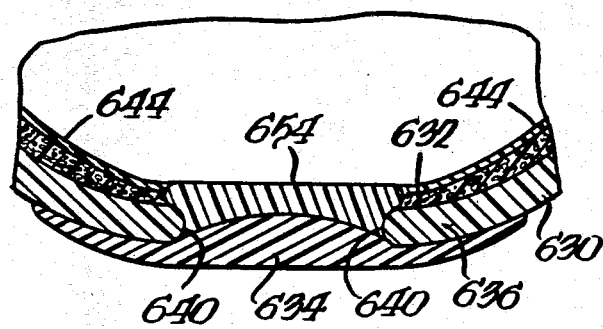
FIG. 8 is a fragmentary cross-sectional view of portions of a cervical cap assembly fitted with a bridge plug and liner sheath for in situ molding and curing in accordance with principles of the present invention.

The method shown in the embodiment of FIG. 8 is substantially similar to the embodiment of FIG. 6 except that a bridge plug or umbrella plug 654 is used in lieu of canal button or plug 450 (FIG. 6). Bridge plug 654 bridges the valve opening 640 and is adhesively attached to the concave inner surface 632 of shell 630 adjacent the valve opening 640. Liner sheath 644 is adhesively attached to bridge plug 654 if not already integrally connected thereto.

Figure 9:
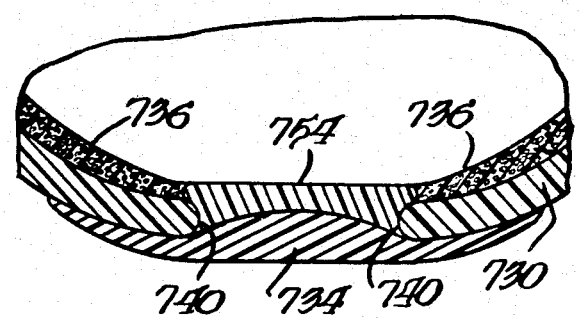
FIG. 9 is a fragmentary cross-sectional view of portions of a cervical cap assembly fitted with a bridge plug for in situ molding and curing in accordance with principles of the present invention.

The method shown in the embodiment of FIG. 9 is similar to that illustrated in FIG. 8, except that no liner sheath is used and the moldable material forming layer 736 directly contacts the exocervical surface of the cervix uteri when the cap assembly is molded and cured in situ.

Figure 10:
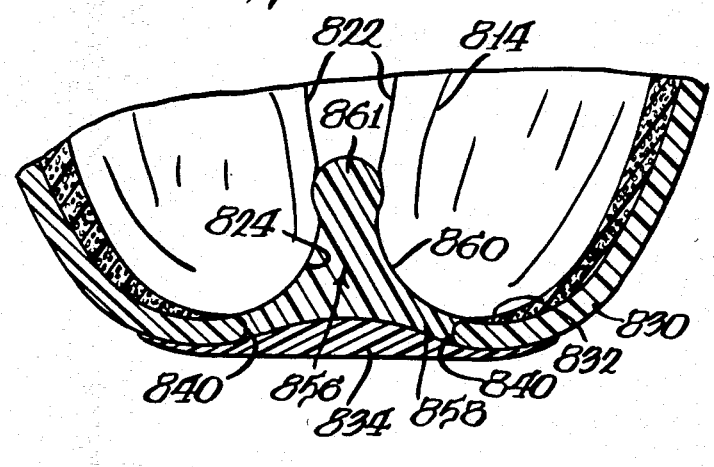
FIG. 10 is a fragmentary cross-sectional view of portions of a cervical cap assembly utilizing a T-plug for in situ molding and curing in accordance with principles of the present invention.

The method shown in embodiment of FIG. 10 is similar to the embodiment of FIG. 9, except that an inverted T-shaped plug or T-plug 856 is used in lieu of bridge plug 754 (FIG. 9) to give stability for the alignment of the internal opening or port of the cap tunnel with the cervical os. T-plug 856 includes base 858 which bridges valve opening 840 and rounded stem 861 having concave sides 860. Stem 861 is contoured to be received into the cervical os 824 and retained in position during molding and curing. The periphery of base 858 is contoured to provide a complementary snap fit engagement with the inner edge of shell 830 defining the valve opening or aperture 840.

Alternatively, a temporary liner sheath can be provided connected to the T-plug 856 of FIG. 10. In such a case the liner sheath as well as plug 856 are removed when the material forming elastomeric layer 836 has been cured.

Plugs and liner sheaths having different shapes and thicknesses can be used without departing from the scope of this invention. Furthermore, it may be desirable in some circumstances, to remove part or all of the liner sheaths 44 in the embodiments above utilizing liner sheaths after the elastomeric-forming material 36 has been cured and the cap assembly removed from the cervix uteri.

The plugs are, of course, sterile when used, and preferably have a configuration approximating that of a dumbell with one end somewhat flattened, as illustrated in FIG. 10 for T-plug 856. Preferably the overall length of the plug is about 15 millimeters and the end of the plug entering the cervical os is about 7 millimeters in diameter.

Figure 11:
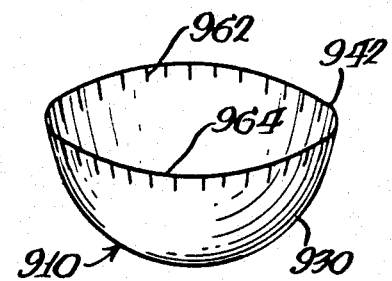
FIG. 11 is a perspective view of a cervical cap assembly having a slit rim with independently movable or deformable rim sections in accordance with principles of the present invention.

As shown in FIG. 11, the rim or skirt 942 of the cap assembly 910 can also be slit, such as at equally spaced circumferential intervals about rim 942 to provide arcuate longitudinal slits 962, i.e., slits along the great circles of longitude of hemispherical shell 30, which form separate bendable rim sections 964. Rim sections 964 assist in preventing the cervical cap assembly from becoming dislodged during vigorous sexual intercourse and strenuous exercises. In some circumstances it may be desirable to attach a separate deformable skirt to the perimeter or rim of the shell. In addition, shell 30 can be tapered or reduced in thickness by mechanical means, to a dimension of about 0.2 mm., after curing and removal, prior to mechanically creating slits 962.

The shell portion of the cervical cap assembly can be made from a wide variety of flexible, non-porous materials such as natural rubber, certain types of silicone rubber that are non-porous when cured, polyurethane, thermoplastic elastomers, such as polyolefin blends, styrene/elastomer block copolymers, copolyesters, and polyurethane block copolymers. Particularly suitable are the styrene/elastomer block copolymers such as those commercially available from the Shell Chemical Company, Oak Brook, Ill., under the designation "Kraton" and "Kraton G" and described in U.S. Pat. No. 3,231,635 to Holden et al. These styrenic thermoplastic elastomers are block copolymers of polystyrene and an elastomer such as polyisoprene, polybutadiene, ethylene-propylene, or ethylene-butylene rubber. While these thermoplastic elastomers differ chemically, their morphology is similar. Blocks or domains of relatively hard thermoplastic constituents link elastomeric constituents in a network that behaves like a chemically cross-linked rubbery structure. At forming temperatures the relatively hard thermoplastic domains of the structure soften and allow the polymeric material to flow. Upon cooling, these relatively hard domains resolidify and re-establish the rubber-like, elastic structure.

Thermoplastic elastomers that exhibit a surface charge provide a further advantage for the present purposes in that the presence of such a charge on the fabricated shell and or the web tends to inhibit sperm motility and may disorient the molecular structure of cervical mucous, inhibiting sperm transit.

The web for the one-way valving means can be made from the same elastomeric material or from a different, non-porous elastomeric material, as the shell, such as natural rubber, silicone rubber, polyurethanes, fluorocarbon rubbers, styrene-butadiene rubbers, and the like. For ease of manufacture it is preferred to have the web of the same elastomeric material as the shell material. The web can be unitary with the shell or integrally bonded to, and thus integral with, the shell. In general, however, the web thickness is selected so as to provide a minimal valve-opening pressure, usually about 5 millimeters of mercury or less.

The sheet-like liner sheath can be made of non-porous medical grade silicone rubber, natural rubber or the like. If to be left in place, the liner sheath should be fluid impermeable, non-porous, smooth and of a wettable material which is non-irritating to cervical tissue. In any event, the cap surfaces should be such as not to harbor undesirable microorganisms.

The plugs can be made of natural rubber, medical grade silicone rubbers or the like.

For cervical cap assemblies having a wettable, non-porous permanent liner sheath defining the contact surface with the cervix uteri, elastomeric layer 36 can be custom molded using a non-wettable medical grade silicone rubber. Physiologically compatible, two-component room temperature vulcanizing or vulcanizable, non-wettable silicone rubber suitable for the present purposes, also referred to as "RTV silicone rubber", is commercially available under the trademark SILASTIC 382 or SILASTIC 502 medical grade elastomer from Dow Corning Corporation. SILASTIC 382 medical grade elastomer consists substantially of an opaque viscous elastomer base of polydimethylsiloxane polymer, silica filler, and stannous octoate as catalyst. Typical properties for Silastic 382 medical-grade elastomer are shown in the table below:

TABLE I

Silastic 382 Medical Grade Elastomer

| Property | Test method | |
|---|---|---|
| Before Catalyzing | | |
| Viscosity, centipoises | | 50,000 |
| After Vulcanizing for 24 Hr. at 77° F. | | |
| Color | | White |
| Specific gravity | | 1.13 |
| Durometer hardness, Shore A | ASTM D676 | 43 |
| Tensile Strength, psi | ASTM D412 | 400 |
| Elongation, % | ASTM D412 | 160 |
| Die B tear strength, psi | ASTM D624 | 25 |
| Brittle point, °F. | ASTM D746 | −100 |
| Shrink, Linear, % | | |
| after 3 days at 77° F. | | 0.4 |
| after 6 days at 77° F. | | 0.6 |
| after 14 days at 77° F. | | 0.7 |
| Water absorption, wt. %, after 7 days immersion at 77° F. | | 0.4 |
| Thermal conductivity, cal/cm °C. sec | | $0.525 \times 10^{-3}$ |
| Volume coefficient of thermal expansion °C. (0 to 100) | | $7.50 \times 10^{-4}$ |

Two-component RTV silicone rubber cures in a relatively short time and is formed by mixing the catalyst into the elastomer base to bring about vulcanization. The elastomer base includes the fluid silicone polymer mixed with filler and a material designed to act as a cross-link. Because of the necessity of mixing in a catalyst, the viscosity of the polymer used must be low enough to permit easy stirring. Also, the fillers used must not thicken too greatly. Medical-grade RTV silicone rubber vulcanized with stannous octoate shows no more tissue reaction than the other medical-grade silicones.

The process of vulcanization of the two component RTV's is as follows. The polymer used has a high degree of hydroxy end-blocking as shown by Formula I:

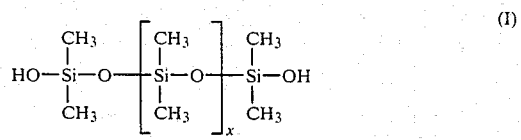

The cross-linking between these polymer chains is accomplished by a material such as propyl orthosilicate shown by Formula II:

$$Si(OCH_2-CH_2-CH_3)_4 \qquad (II)$$

When the stannous octoate catalyst is stirred into a mixture composed of the compound of Formula II and a hydroxy end-blocked silicone polymer of the type shown by Formula I, the hydroxyl on the end of the polymer reacts with the alkyl group, forming an alcohol. The polymer chain then attaches to the silicate as shown below, forming the network necessary for a material to have rubbery properties is formed.

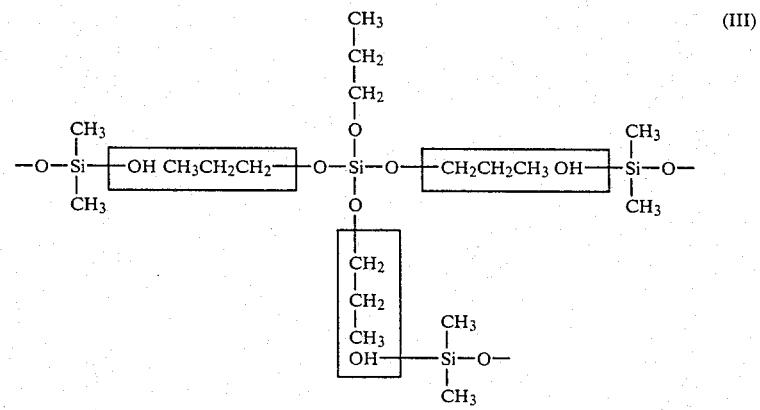

The RTV silicone rubber is formed into a moldable paste-like composition and is inserted into the space between inner surface 32 of shell 30 and liner sheath 44 during formation of cap assembly 10. The mixture is poured in the presence of a setting agent into the pocket between the concave inner surface 32 of the shell 30 and the liner sheath 44 at ambient room temperature or at a temperature at about body temperature of the women for whom the cap is made as described above with respect to FIGS. 1–8 or between the concave inner surface 32 of the shell 30 and the exocervical surface 12 of the cervix uteri 14 at about body temperature as described above with respect to FIGS. 9 and 10. The cap assembly is then inserted against the exocervical surface 12 of the cervix uteri 14 as described above, so that the elastomeric composition will cure and set in situ to form a coherent, exocervical surface-conforming, pliable resilient layer. The preferred elastomeric composition should be molded and cured in situ in a relatively short time, such as in less than 15 minutes and preferably within three or four minutes.

Before introducing the elastomeric material 36 into the pocket between liner sheath 44 and the concave inner surface 32 of shell 30, it may be desirable in some circumstances to wash the inner surface of the shell with a solution of a strong mineral acid, such as hydrochloric acid, or to prime the surface with a dispersion made from a medical adhesive silicone, such as sold under the trademark SILASTIC medical adhesive silicone Type A, in dry aromatic, aliphatic or chlorinated hydrocarbon solvents. Alternatively, a mesh or screen can be connected to the inner surface of the shell to secure the elastomeric material to the cap. Furthermore, it may be desirable in some cases to pre-fill the cavity or pocket between liner sheath 44 and shell 30 and to inject the catalyst through the liner sheath into the elastomeric-forming material in the pocket at the time of use.

The moldable elastomeric material can also be formed as described in Examples 1-3 below:

EXAMPLE 1

|  | Parts by weight |
|---|---|
| Room temperature vulcanizing silicone rubber (Silastic RTV 502), a liquid prepolymer dimethyl silicone, about 45,000 cs | 30 |
| Silicone rubber foam (Silastic Q-3-0030), intumescent, about 5,000 cs | 30 |
| Cyclic dimethylpolysiloxane (silicone fluid), 20 cs | 40 |
| Stannous octoate (catalyst) | 2 |

The viscosity of the material, immediately after the catalyst is added, and before setting begins appreciably, is less than 6,000 centistokes.

In using the composition of Example 1, the catalyst is added immediately before the material is used. The material can be put into a flexible, liquid impervious bag and mixed.

EXAMPLE 2

|  | Parts by weight |
|---|---|
| Room temperature vulcanizing silicone rubber (Silastic RTV 502), a liquid prepolymer dimethyl silicone, about 45,000 cs | 50 |
| Silicone rubber foam (Silastic Q-3-0030), intumescent, about 5,000 cs | 50 |
| Cyclic dimethyl polysiloxane (silicone fluid), 20 cs | 2 |

The viscosity of the material, immediately after the catalyst is added, and before setting begins appreciably, is less than 6,000 centistokes.

EXAMPLE 3

The following ranges of the silicone ingredients of Example 1 and 2 are operative. Other proportions may be useful.

|  | Parts by weight |
|---|---|
| Silastic RTV 502 | 10-40 |
| Silastic Q-3-0030 | 70-30 |
| Silicone fluid | 5-40 |

In any of Examples 1, 2 and 3, other RTV silicone rubbers and silicone fluids may be used. The "Silastic" products are commercially available from Dow Corning Corporation. Other suitable RTV silicone rubbers are commercially available from General Electric, designated RTV 11 and RTV 40, and RTV 120 and RTV 160 respectively. These latter are also curable with stannous octoate.

Another suitable silicone elastomer for the foregoing purposes is Silastic 390, available as a two-component, self-curing system under the designation "Prolastic 35" from Prolastic Co., Inc., Rochester, N.Y.

Where the liner sheath 44 is removed after curing and in those cases where it is desired to cure and mold the elastomeric layer directly in contact with the cervix, the elastomeric layer should provide a wettable, non-porous contact surface. In instances where the elastomeric layer is comprised of a silicone rubber, wettability can be achieved by combining with the silicone prepolymer a predetermined amount of hydroxyethyl-methacrylate, curing the prepolymer in the usual manner, and thereafter subjecting the obtained material to gamma-radiation. In lieu of the hydroxyethylmethacrylate, polymerizable vinyl-group containing monomers such as acrylic acid, alkali metal acrylates, vinyl pyrrolidone, or the like can be used.

Elastomeric foams such as silicone elastomer foam, flexible urethane foam and cross-linked polyethylene foam can also be used to form at least a portion of the elastomeric layer 36 as long as appropriate steps are taken to avoid fluid penetration therein, e.g., by using a liquid impervious, nonporous liner sheath to define the exposed or contact surface of the elastomeric layer, by forming a liquid impervious skin for the elastomeric layer, or the like.

Suitable elastomeric silicone foams can be prepared by mixing an organohydrogensiloxane, a hydroxylated organosiloxane, and a platinum catalyst in amounts to provide a ratio of silicon-bonded hydrogen atoms to silicon-bonded hydroxyl radicals of about 2.5 to about 40 and thereafter permitting the mixture to foam.

Suitable flexible urethane foams can be prepared by reacting relatively high molecular weight polyols with isocyanates.

High-resilience foams, with a sag factor (the ratio of the load needed to compress foam by 65% to the load needed to compress foam by 25%) of 2.7 and above, preferably in the range between about 3 to about 3.2 are particularly useful where foams are used to form the elastomeric layer.

High-resilience polyurethane foams are prepared by reacting an isocyanate mixture constituted by about 80 percent 80/20 tolylene diisocyanate ("80/20" refers to the ratio of the isomeric 2,4-tolylene diisocyanate to 2,6-tolylene diisocyanate) and about 20 percent polymethylenepolyphenyl isocyanate with a polyether triol having a molecular weight of about 4500 to about 6000 and made by reacting ethylene oxide with polypropylene oxide-based triols. Diol extenders such as methyl-diethanol-amine, which also acts as a catalyst, can also be used in making high resilience foams.

Other materials can also be used to form the elastomeric layer.

Although specific embodiments of the invention have been shown and described, it is to be understood that various modifications and substitutions, as well as rearrangement of parts and steps, can be made by those skilled in the art without departing from the spirit and scope of this invention.

We claim:

1. A cervical cap assembly, comprising:
   a flexible shell having a concave inner surface and one-way valving means operatively associated with said shell for permitting egress of uterine discharges but preventing ingress of sperm; and
   a liquid impervious, non-porous elastomeric lining on said concave inner surface defining a wettable, matingly fitting and resiliently complementing contact surface permanently contoured for the exocervical surface of a cervix uteri.

2. A cervical cap assembly in accordance with claim 1 wherein a flexible skirt depends from said shell.

3. A cervical cap assembly in accordance with claim 2 wherein said flexible skirt is provided with a plurality of spaced slits.

4. A cervical cap assembly, comprising: a flexible, non-porous shell having a concave inner surface and one-way valving means for permitting egress of uterine discharges but preventing ingress of sperm;
   a flexible, liquid impervious, non-porous liner sheath connected to said shell for positioning against the exocervical surface of a cervix uteri; and
   an intermediate resilient elastomeric cushion positioned between said concave inner surface and said liner sheath, said cushion having an exocervical-fitting permanently contoured surface adjacent said liner sheath for matingly fitting and resiliently complementing the exocervical surface of the cervix uteri.

5. A cervical cap assembly in accordance with claim 4 wherein a portion of said liner sheath is detachable.

6. A cervical cap assembly in accordance with claim 4 wherein said liner sheath includes a flexible sheet generally covering and conforming to the shape of said exocervical-fitting contoured surface.

7. A cervical cap assembly in accordance with claim 4 wherein said liner sheath and said cushion are of the same material.

8. A cervical cap assembly in accordance with claim 4 wherein said cushion and said shell are of the same material.

9. A cervical cap assembly in accordance with claim 4 wherein said cushion is a room temperature vulcanizing silicone rubber.

10. A cervical cap assembly in accordance with claim 4 wherein said cushion is an elastomeric foam.

11. A cervical cap assembly in accordance with claim 10 wherein said cushion is a silicone foam.

12. A cervical cap assembly in accordance with claim 10 wherein said cushion is a urethane foam.

13. A cervical cap assembly in accordance with claim 4 wherein said shell has a tapered body.

14. A cervical cap assembly in accordance with claim 4 wherein said shell has separately bendable rim sections.

15. A cervical cap assembly in accordance with claim 4 wherein said liner sheath has arcuate end portions adjacent said rim.

16. A cervical cap assembly in accordance with claim 15 wherein said liner sheath is bent over said rim.

17. A cervical cap assembly in accordance with claim 4 wherein said elastomeric cushion has a reduced thickness adjacent said rim.

18. A cervical cap assembly in accordance with claim 4 wherein said elastomeric cushion has frusto-conical end portions extending beyond said shell.

* * * * *